US007771356B2

(12) United States Patent
Voie et al.

(10) Patent No.: US 7,771,356 B2
(45) Date of Patent: Aug. 10, 2010

(54) ULTRASOUND TYMPANOSCOPE

(75) Inventors: Arne H. Voie, Seattle, WA (US); Mark A. Moehring, Seattle, WA (US); George A. Gates, Woodway, WA (US); Eugene A. Saxon, Seattle, WA (US); Mailee J. Hess, Portland, OR (US)

(73) Assignee: Spentech, Inc., Seattle, WA (US)

( * ) Notice: Subject to any disclaimer, the term of this patent is extended or adjusted under 35 U.S.C. 154(b) by 260 days.

(21) Appl. No.: 11/274,729

(22) Filed: Nov. 14, 2005

(65) Prior Publication Data

US 2007/0129632 A1 Jun. 7, 2007

(51) Int. Cl.
*A61B 8/00* (2006.01)
(52) U.S. Cl. .................................... 600/438; 600/437
(58) Field of Classification Search ......... 600/437–461, 600/300; 604/19, 20, 606, 601
See application file for complete search history.

(56) References Cited

U.S. PATENT DOCUMENTS

| 5,711,308 | A | * | 1/1998 | Singer | 600/559 |
| 5,792,072 | A | * | 8/1998 | Keefe | 600/559 |
| 6,093,150 | A | * | 7/2000 | Chandler et al. | 600/459 |
| 6,216,040 | B1 | * | 4/2001 | Harrison | 607/57 |
| 7,131,946 | B2 | | 11/2006 | Lewandowski | 600/438 |
| 2004/0138561 | A1 | * | 7/2004 | Lewandowski et al. | 600/437 |
| 2004/0167404 | A1 | | 8/2004 | Bessler | 600/443 |
| 2004/0230124 | A1 | * | 11/2004 | Querfurth | 600/485 |

OTHER PUBLICATIONS

Abramson, D.H. et al., "Ultrasonics in Otolaryngology", Arch Otolaryng, vol. 96, Aug. 1972. pp. 146-150.
Alvord, L.S. et al., "Real-time B-scan Ultrasound in Middle Ear Assessment", American Institute of Ultrasound in Medicine, J Ultrasound Med 9:91-94, 1990. pp. 91-94.
Alvord, L.S., "Uses of Ultrasound in Audiology", Journal of the American Academy of Audiology, vol. 1, No. 4, Oct. 1990. pp. 227-235.
Discolo, C.M. et al., "Ultrasonic Detection of Middle Ear Effusion", Arch Otolaryngol Head Neck Surgery, vol. 130, Dec. 2004. pp. 1407-1408.
Wu, Chih-Hsiu et al., "Preliminary Use of Endoluminal Ultrasonography in Assessment of Middle Ear with Effusion", American Institute of Ultrasound in Medicine, J Ultrasound Med 17:427, 1998. pp. 427-430.

* cited by examiner

*Primary Examiner*—Brian Casler
*Assistant Examiner*—Elmer Chao
(74) *Attorney, Agent, or Firm*—Dorsey & Whitney LLP

(57) ABSTRACT

A system and method for examining a patient for an ear disorder. Reflectance ultrasound is applied to a portion of the ear to determine the presence of ear effusion in a middle ear. If ear effusion is present, motion of the tympanic membrane is induced and ultrasound is further applied to the moving tympanic membrane. Echo signals resulting from the ultrasound applied to the moving tympanic membrane are analyzed to obtain information regarding the motion of the tympanic membrane and is used to characterize the ear effusion.

22 Claims, 10 Drawing Sheets

ULTRASOUND TYMPANOSCOPE

STATEMENT AS TO GOVERNMENT RIGHTS

The disclosed invention was made with support from the United States Government, which has certain rights in the invention pursuant to Grant No. 1R 43DC007013-01 awarded by the National Institutes of Health.

TECHNICAL FIELD

This invention relates generally to medical ultrasound apparatus and methods, and more particularly, to a ultrasound system and method for evaluating ear disorders.

BACKGROUND

Otitis media ("OM"), is the most common cause of childhood health issues, which include for example, bacterial infections, antibiotic prescriptions, hearing loss, and surgeries (after circumcision). OM is responsible for more than 16 million office visits nationwide per year, accounting for over 50 percent of all pediatric antibiotic prescriptions and as much as $5 billion in annual costs. The number of operative procedures performed due to OM in the United States is estimated at about 600,000 per year.

The majority of children have at least one episode of acute OM ("AOM") by the time they are two years of age. AOM is characterized by ear pain, fever, occasional rupture of the ear drum, and findings of middle ear inflammation, including liquid in the middle ear. About 10 percent of children have recurrent AOM, and these children account for around 40 percent of all AOM episodes. The prevalence of OM in the United States is increasing. Thus, current diagnostic and treatment methods are not lowering the rate of OM in the United States.

OM is fundamentally defined by the presence of a liquid effusion in the middle ear. In AOM, the middle ear effusion ("MEE") is induced by infective agents and is often thin or serous with viral infection and thicker and purulent with bacterial infection. Acute MEE may persist, even with appropriate antimicrobial treatment. After 30 days, the MEE is termed as chronic, and the condition is referred to most commonly as otitis media with chronic effusion or "OME." Chronic MEE may be thin and watery, purulent, or, most commonly, thick and mucoid. Mucoid effusion is the hallmark of OME and is often called "glue ear" because of its viscosity. Because each type of MEE has a different prognosis and treatment, the ability to delineate the type of the effusion is of great clinical value.

In spite of decades of research, optimal management of OM remains controversial. In a recent prospective study, antibiotic treatment of OM accounted for more than 90 percent of all antibiotic use during the first two years of life. It has been estimated that distinguishing AOM from OME, and deferring antibiotics for OME, would avoid 6 to 8 million courses of unnecessary antibiotic therapy annually. While antibiotics reduce pain symptoms in AOM, their widespread use in AOM—many say overuse—has led to an alarming increase in the prevalence of resistant organisms worldwide without any substantial decrease in complications or sequelae of AOM. Given the high spontaneous resolution rate of AOM, there are serious questions about the need for antibiotics in most or even all cases. Thus, physicians and parents are frequently uncertain about proper treatment because there are no clear-cut clinical findings that might reliably predict which cases will resolve spontaneously and which cases would be better treated with an oral antibiotic.

Add to this the problem of over-diagnosis of MEE owing to technical problems, as will be described below. Many children with fever and a red tympanic membrane ("TM") have no MEE and thus do not have AOM. These children do not benefit from antimicrobial therapy, even though many receive it as a precaution.

Similar considerations apply to cases of persistent MEE (OME). Detecting MEE is difficult without expensive equipment, such as a tympanometer or an audiometer. While screening tympanometers are available, they are not widely used in primary care offices where the majority of cases of AOM/OME are first seen. Acoustic reflectometry was introduced 15 years ago as a method for primary physicians and parents to indicate MEE presence. Although the sensitivity and specificity of acoustic reflectometry is similar to that of tympanometry, neither device will predict which cases may resolve spontaneously and which cases will require treatment. Moreover, neither device is widely used in primary care offices. Chronic MEE is therefore under-diagnosed in primary care practice.

OME may cause hearing loss without other symptoms. The adverse effects of OME on hearing and on the development of cognitive, linguistic, auditive, and communicative skills are of concern to parents and physicians alike. National guidelines recommend waiting 3 to 6 months before surgical removal of the MEE and insertion of a ventilation tube. Some effusions cause substantial hearing loss, while in other cases hearing may be nearly normal. Typically, middle ears that are impacted with the characteristic viscous effusion (glue ear) are associated with substantial hearing loss that may persist for years. No existing clinical method can distinguish between a mucoid effusion (glue ear) and one that contains a serous (watery) effusion, which is more likely to resolve spontaneously.

One of the major sources of controversy about OM in clinical practice is accuracy of diagnosis. Otoscopy, the key examination technique, is a visual inspection of the TM by which one may deduce the normal or abnormal middle ear. The equipment and skills for otoscopy are variable. Although with practice, many physicians become proficient otoscopists, it is fair to say that monocular examination of the TM of a struggling infant through a tiny speculum remains a difficult and challenging maneuver. Often only a glimpse of the TM is possible. Use of the binocular operating microscope, which permits a 3D view of the TM, is the most precise method of otoscopy and is widely used by ears, nose, and throat specialists. However, this expensive equipment is rarely found in primary care practices where the majority of AOM diagnoses are made. Unfortunately, only 40 percent of primary care pediatricians are confident about their otoscopic findings.

The essential elements of otoscopy are a description of: (1) the static characteristics of the TM (color, position, translucency), (2) the contents of the middle ear (air, ear effusion, other), and (3) the mobility of the TM in response to externally applied air pressure (pneumatic otoscopy). Determining the presence of effusion (liquid) in the middle ear is the critical variable in making a diagnosis of OME. Given that the effusion may vary in amount and consistency from case to case and may be obscured by the condition of the TM, it is fair to say that even when done under ideal conditions (binocular microscope, pneumatic speculum, and an anesthetized child), the otoscopic conclusion regarding the presence or absence of ear effusion may vary from observer to observer. Less than half of pediatricians use pneumatic otoscopy. Similar findings have been found in surveys of practicing physicians and residents.

Tympanometry is an objective measure of the condition of the middle ear. It is widely used in specialty clinics for screening and for diagnostic confirmation. The tympanometer displays the change in the acoustic immittance of a 226 Hz transducer tone as the pressure in the ear canal is varied from −300 to +200 daPa. The classic peaked curve indicates an air-containing middle ear while a classic flat curve is associated with middle ear effusion (assuming an intact TM). Tympanometry is not widely used in primary care offices because of equipment expense and training requirements. The test does require a snug fit between the probe and the ear canal; fitting tightly is not objectionable for older or normal children. However, the pressurization may cause mild discomfort in the presence of an acute infection.

Audiometry often reveals a substantial conductive hearing loss in OME. However, audiometry is expensive and not widely available. Infants and children are not difficult to test by experienced audiologists. However, hearing may vary from day to day. Audiometry is important in surgical planning but is too non-specific for evaluation of effusion type because the volume more than the nature of the effusion, is responsible for the degree of hearing loss.

Acoustic reflectometry (measuring response of the TM to a 1.8 to 4.4 kHz frequency sweep spectrum) was introduced to meet the need for an objective, simple, and safe clinical method for evaluating the condition of the middle ear. While acoustic reflectometry is indeed simple, safe, and inexpensive, it is too unreliable for making treatment decisions and is used infrequently by physicians.

More recently, processes for determining ear effusion viscosity using ultrasound have been described in U.S. Patent Application Publications 20040133108, 20040138561 and 20040167404. The processes described in these patent applications are based on well understood principles and instrumentation. Reports in the literature concerning analysis of reflected echoes from the TM and middle ear structures date to 1972. See Abramson et al. Ultrasonics in otolaryngology. An aid in the diagnosis of middle ear fluid. *Arch Otolaryngol.* 1972 August; 96(2):146-50. Generally, the processes extend the analysis of these echo-amplitudes to discern viscosity of the middle ear effusion to identify the type of effusate. However, the transducers and applied signals have been used to interrogate the TM environment in this context previously. See Alvord. Uses of ultrasound in audiology. *J Am Acad Audiol.* 1990 October; 1(4):227-35. Review., Alvord et al. Real-time B-scan ultrasound in middle ear assessment. A preliminary report. *J Ultrasound Med.* 1990 February; 9(2): 91-4.; Wu et al. Preliminary use of endoluminal ultrasonography in assessment of middle ear with effusion. *J Ultrasound Med.* 1998 July; 17(7):427-30.

Given that the vast majority of cases of AOM are seen initially in emergency rooms and primary care practices, and, further, that these facilities lack equipment for sophisticated evaluation and diagnosis, it is fair to say that a reliable, simple to use, and relatively inexpensive instrument with superior evaluative responsiveness could change the health care of infants and children with AOM/OME. Specifically, antibiotic prescriptions would be decreased, specialty referrals could be limited to those with truly persistent mucoid effusions, and primary care physicians would be empowered to evaluate, treat, and follow-up their own cases.

SUMMARY

An aspect of the invention provides a method and system for analyzing motion of the tympanic membrane including applying ultrasound to a moving tympanic membrane, and analyzing echo signals resulting from the ultrasound to obtain information regarding the motion of the tympanic membrane.

Another aspect of the invention provides a method and system for examining an ear of a patient. The method includes applying ultrasound to a portion of the ear and detecting the presence of a substance in the middle ear from reflected ultrasound. If a substance is detected, a motion response of a tympanic membrane is analyzed and the substance is categorized based on the motion response analysis.

Another aspect of the invention provides method and system for examining a patient for an ear disorder. The method includes applying reflectance ultrasound to determine the presence of ear effusion in a middle ear and applying Doppler ultrasound to characterize the ear effusion if present.

Another aspect of the invention provides an ultrasound system and method for examining an ear of a patient. The system includes an ultrasound probe operable to provide ultrasound to a portion of the ear and receive echo signals therefrom and an ultrasound signal processing circuit operable to process the echo signals to detect the presence of a substance in the middle ear, and if a substance is detected, analyze motion response of a tympanic membrane in motion to characterize the detected substance.

Another aspect of the invention provides an ultrasound probe for examining an ear of a patient. The probe includes a housing configured to fit in an ear canal and an aperture in the housing through which a liquid is introduced into the ear canal. A valve through which the liquid is removed from the ear canal and a transducer positioned in the housing and operable to provide ultrasound to a portion of the ear are also included as part of the probe.

DETAILED DESCRIPTION

Certain details are set forth below to provide a sufficient understanding of the invention. However, it will be clear to one skilled in the art that the invention may be practiced without these particular details. Moreover, the particular embodiments of the present invention described herein are provided by way of example and should not be used to limit the scope of the invention to these particular embodiments. In other instances, well-known circuits, control signals, timing protocols, and software operations have not been shown in detail in order to avoid unnecessarily obscuring the invention.

Figure 1:
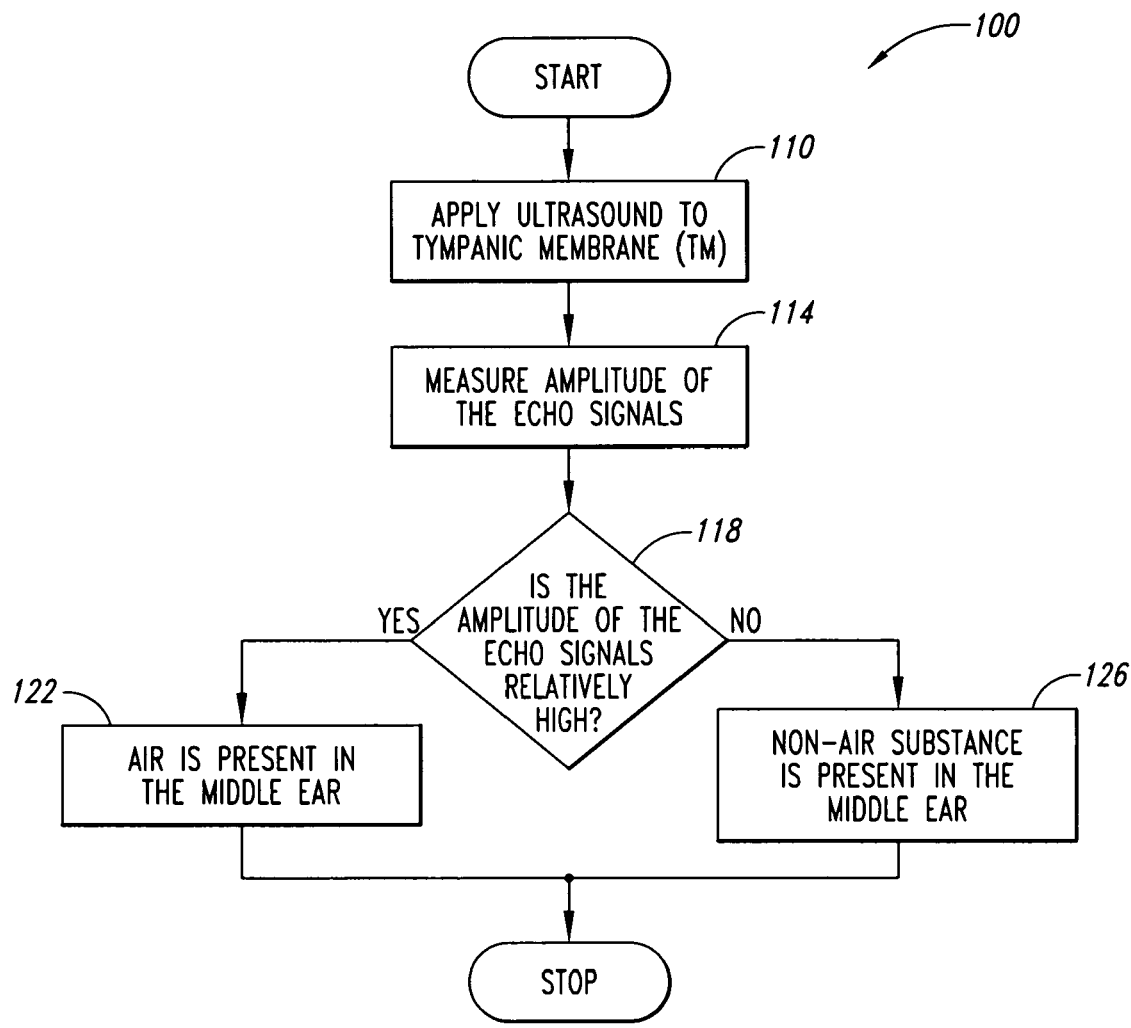
FIG. 1 is a flow diagram for determining the presence of air or a substance other than air in the middle ear of a patient in accordance with an embodiment of the invention.

FIG. 1 illustrates a process 100 for determining whether air or a substance other than air is present in the middle ear. Examples of "non-air" substances include a liquid, such as middle ear effusion, and tissue, such as from a tumor. The following description specifically refers to the non-air substance as an ear liquid. However, this is provided by way of a non-limiting example. Alternative embodiments of the present invention can be used in applications involving substances other than, or in addition to, ear liquid.

Reflectance ultrasound is used in the process 100 for making the determination of air or non-gas substance present in the middle ear. At step 110 ultrasound is delivered to the tympanic membrane of a patient. Conventional acoustic coupling media can be used for coupling the ultrasound to the tympanic membrane, for example, saline, acoustic gel, water or the like. In an alternative embodiment, an air conduction medium is utilized to couple ultrasound to the tympanic membrane. The specific coupling media described herein have been provided by way of example, and are not intended to limit the scope of the present invention. As will also be described in more detail below, the ultrasound probe used to deliver the ultrasound to the tympanic membrane preferably has a form factor to allow the transducer to partially fit in the ear canal of the patient. For example, a transducer having an active element diameter of approximately 3 mm is anticipated to be suitable, however, other sized transducers can be used as well.

At step 114 echo signals received by the ultrasound transducer are processed to provide reflectance data, which includes data for the amplitude of the echo signals. The data for the amplitude is analyzed, and a determination is made at step 118 whether the amplitude of the echo signals is indicative of the presence of air or liquid, such as effusion, in the middle ear. Generally, echo signals having a relatively high amplitude are indicative of the presence of air in the middle ear (step 122). In contrast, echo signals having a relatively low amplitude is indicative of the presence of ear effusion in the middle ear (step 126).

A thresholding technique can be used to determine whether the amplitude is indicative of air or ear effusion in the middle ear. For example, where the amplitude of the echo signals exceeds a first threshold, the echo signals are interpreted as indicating the presence of air, and where the amplitude of the echo signals is less than a second threshold, the echo signals are interpreted as indicating the presence of ear effusion. The first and second thresholds can be different to provide multiple confidence levels, or to distinguish between air and substances other than ear effusion, such as other liquids or tissue. Alternatively, one threshold (i.e., the first and second thresholds are equal) can be used for a binary determination of the presence of air or ear effusion. In addition to a thresholding technique, other techniques for making a determination based on the amplitude of the echo signals can be used as well.

Figure 2:
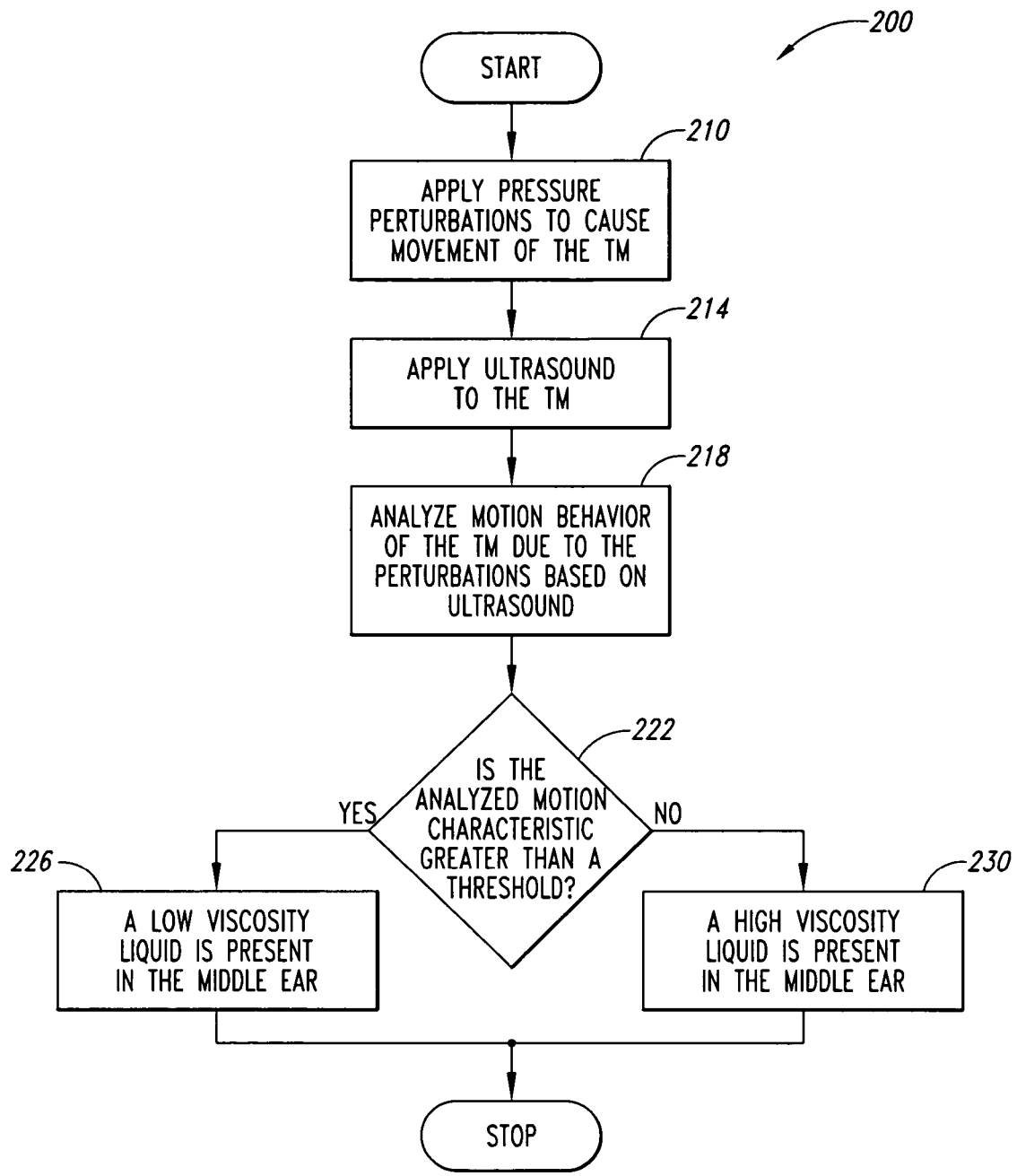
FIG. 2 is a flow diagram for using Doppler ultrasound to analyze motion of the tympanic membrane of a patient in accordance with an embodiment of the invention.

FIG. 2 illustrates a process 200 for using ultrasound to analyze motion of the tympanic membrane in response to perturbation. The process 200 can be used after a determination has been made that ear effusion is present in the middle ear. In one embodiment, processes 100 and 200 are combined to provide a comprehensive middle ear analysis. The results of the analysis constitute findings which inform a physician who will interpret the findings, come to a diagnosis, and determine appropriate clinical management based on the diagnosis. For example, based on the results of the analysis, a physician may be able to determine whether the motion of the tympanic membrane is indicative of acute otitis media or otitis media with effusion.

The analysis begins at step 210 by applying pressure perturbations in the ear canal to induce movement of the tympanic membrane. In one embodiment, pulsed ultrasound is applied to the tympanic membrane at step 214 and Doppler ultrasound processing is used in step 218 to extract Doppler shift signals, which are used to analyze the motion of the tympanic membrane in response to the perturbations. Through Doppler ultrasound processing, different aspects of the motion can be analyzed, individually or in combination, and used for characterizing the tympanic membrane motion. For example, the velocity of the tympanic membrane can be determined using Doppler ultrasound processing, as well as the Doppler displacement (integrated velocity).

Based on the motion characteristic or characteristics analyzed, a determination can be made at step 222 whether the motion of the tympanic membrane is indicative of a relatively low viscosity ear effusion in the middle ear (step 226) or a relatively high viscosity ear effusion in the middle ear (step 230). Generally, in the case where Doppler displacement of the tympanic membrane is analyzed, a relatively high displacement is associated with the presence of a relatively low viscosity ear effusion in the middle ear and a relatively low displacement is associated with the presence of a relatively high viscosity ear effusion in the middle ear. Similarly, a relatively high velocity is associated with the presence of a relatively low viscosity ear effusion and a relatively low velocity is associated with the presence of a relatively high viscosity ear effusion.

While the process 200 has been described utilizing Doppler processing of ultrasound echoes from the tympanic membrane, and a transducer and beam generating capability that will work well with narrow band pulses (i.e., they have many cycles per transmitted burst), "imaging" or short-pulse ultrasound can be used in alternative embodiments. That is, localization of tympanic membrane location can also be accomplished with high resolution using an imaging style ultrasound pulse (approximately 1 cycle per transmit burst) and processing many gate depths simultaneously. In such an embodiment, tracking of the tympanic membrane tissue echo over time can be done by observing the tympanic echo signature versus both depth and time and watching tympanic membrane motion behavior during applied challenges as described elsewhere in this specification.

The process 200 as shown in FIG. 2 uses a thresholding technique at step 222 for characterizing the response of the tympanic membrane to the pressure perturbations. When applying a thresholding technique, a single threshold can be used for a binary characterization of the motion, as shown in FIG. 2, or multiple threshold values can be used as well. Where multiple threshold values are utilized, different levels of motion characterization can be provided.

An experiment was performed using a phantom of a human external ear and middle ear space. Saline and honey were used to simulate ear effusion of two different viscosities. The phantom was composed of three primary pieces, fabricated from hardened resin. A bottom-most piece contained the middle ear space. The space was designed to have a volume of approximately 1 ml, consistent with human anatomical measurements. A rounded structure on the floor of the middle ear space was designed to mimic the promontory of the cochlea, which in situ is situated on the medial wall and projects laterally in the direction of the TM. Mimicking this anatomical feature was believed to be important since ultrasound projected through the TM would likely reflect from this structure and appear as a strong echo signal in the case of a liquid-filled middle ear. Fill and vent ports were also incorporated into the bottom-most piece of the phantom to facilitate the introduction and drainage of experimental middle ear liquids. An upper portion of the bottom-most piece included an opening designed to mimic the transition to the external ear canal. A piece of polyethylene plastic material was used to mimic the TM, which was placed over the TM opening and held in place with an o-ring. Three thicknesses of TM-mimicking material were used: 50 microns, 100 microns, and 200 microns, in order to span the range of normal and inflamed TM.

A middle plastic piece of the phantom was designed to emulate the bony portion of the external ear canal, and also to help hold the TM material in place. This portion of the external canal was designed to be about 10 mm in length, with a diameter consistent with adult human anatomy. A conscious decision was made to place the malleus external to the TM material, as opposed to the interior as would be the case in vivo. In the external position, the malleus can apply pressure to the TM material and push it down into the conical shape of the real TM. The position of the malleus piece, whether internal or external to the TM, was considered unimportant with respect to the ultrasound signal.

A topmost piece of the phantom mimicked the cartilaginous portion of the external ear canal. This piece also held and allowed for aiming of the ultrasound transducer. A fill port allowed saline to be introduced via pressure tubing, filling the entire external ear canal from the TM outward. The transducer was then inserted into the topmost piece to the appropriate depth, and secured in place with a nut, which also completed the seal of the external volume. The entire piece could be translated in order to aim the transducer to achieve the best signal from the TM.

The saline-filled tubing was connected to a variable speed peristaltic pump, which produced the pressure perturbations. The tubing was terminated with a pressure transducer, which monitored the pressure using PowerLab data acquisition software. Experiments were conducted with the 3.5 and 7.5 MHz transducers using a pulse length of 6 cycles. As previously mentioned, three thicknesses of TM material were used: 50, 100, and 200 microns. Also, three types of middle ear substances were used. Air was used to simulate the normal middle ear, and saline was used to simulate the thin effusate associated with AOM, and honey was used to mimic the viscous properties of OME.

A variable speed roller pump applied pressure perturbations to the tubing used to fill the external ear space with saline. This space was sealed so that the pressure changes caused a small movement of the TM material. This movement was in turn processed from the Doppler shift contained in the reflected ultrasound pulse.

The experimental cycle defined above, using 3.5 and 7.5 MHz, was repeated two times and measurements were averaged. The difference in the Doppler (integrated velocity) displacement signal between saline and air were ambiguous. However, a distinction was seen between the two types of liquids. When saline was in the middle ear space, the membrane traveled an average displacement ranging from 12.6 to 31 μm depending on the thickness of the membrane. When the same pressure perturbations were introduced to the ear model with honey in the middle ear, the tympanic membrane traveled an average displacement of 3.75 to 9 μm depending on membrane thickness. Results for all three membrane thicknesses show that smaller TM motions were uniformly observed in association with the thick liquid, while larger TM motions were uniformly observed in association with the thin liquid. Based on the results, it was extrapolated that even though tympanic membrane thickness can vary from person to person, thick liquid behind a thin membrane will not be confused with thin liquid behind a thick membrane. Additionally, it was concluded that when liquid is present in the middle ear space, Doppler ultrasound can distinguish between thin and thick effusates.

Figure 3:
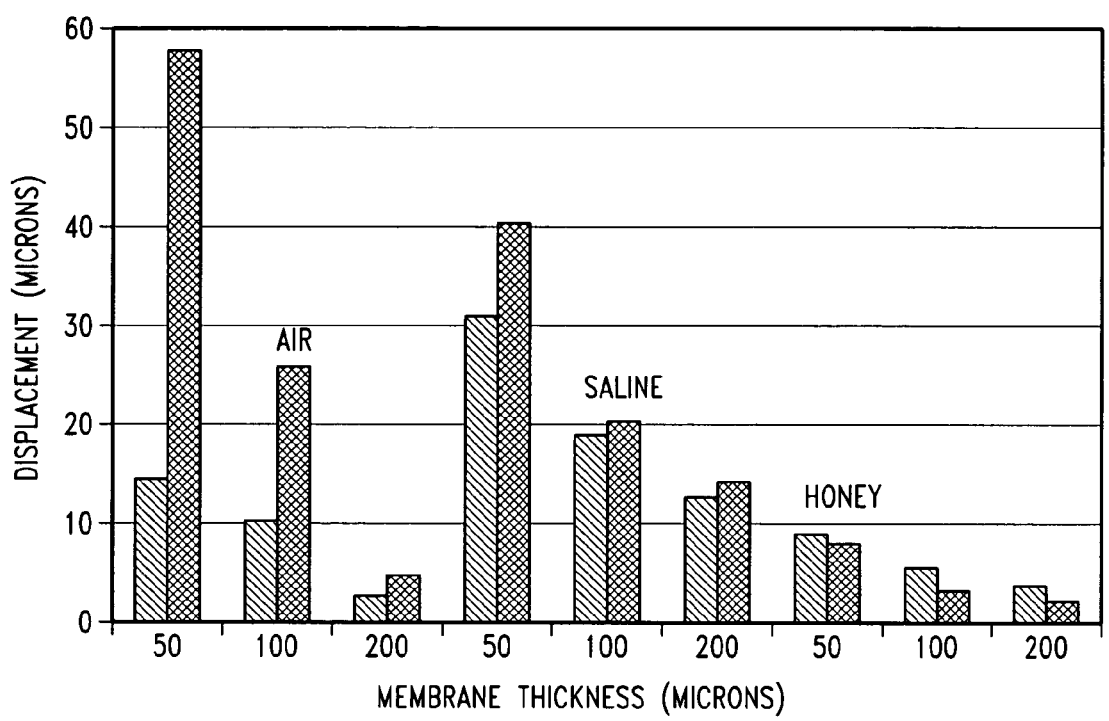
FIG. 3 is a chart summarizing experimental results of using Doppler ultrasound to analyze motion of a simulated tympanic membrane in a phantom of a human external ear and middle ear space.

FIG. 3 summarizes the results of the experiment. Membrane displacement from Doppler processing is along the vertical axis. Three membrane thicknesses, 50, 100, and 200 microns, for air, saline, and honey are shown along the horizontal axis. The results for 3.5 MHz ultrasound is depicted in gray and for 7.5 MHz is depicted in black. As shown in FIG. 3, saline and honey are distinguishable from each other for both frequencies.

Figure 4A:
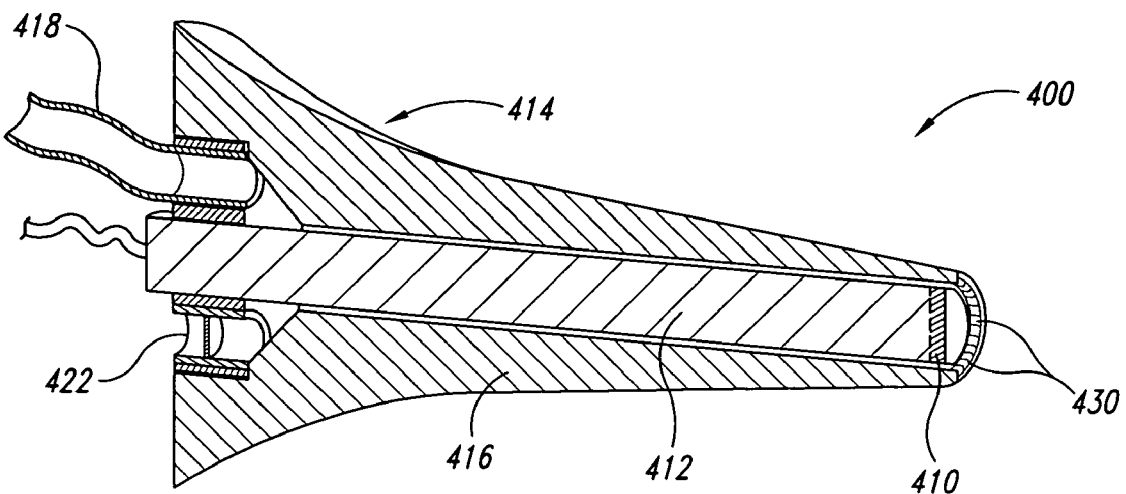
FIG. 4A is a cross-sectional view of a speculum probe according to an embodiment of the invention.
Figure 4B:
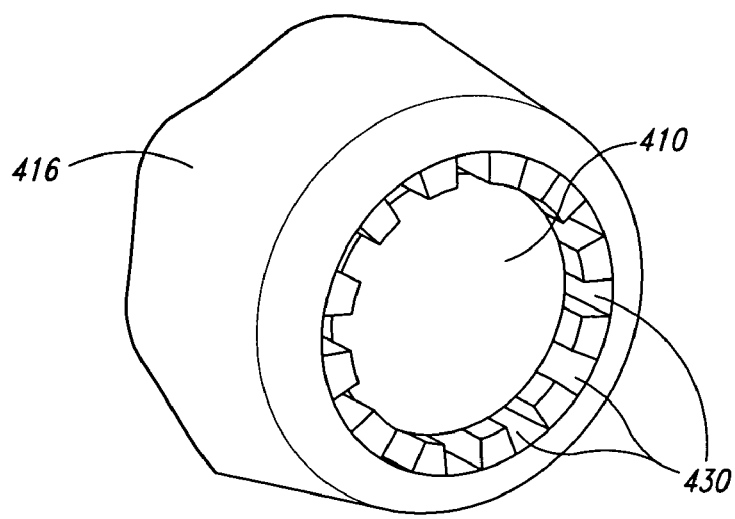
FIG. 4B is a diagram of the tip of the speculum probe of FIG. 4A.

As previously discussed, the process 200 uses Doppler ultrasound to analyze motion of the tympanic membrane in response to pressure perturbations. FIGS. 4A and 4B illustrate an ultrasound speculum probe 400 according to an embodiment of the invention that is configured for providing pressure perturbations and is suitable for Doppler ultrasound analysis of the perturbed tympanic membrane. FIG. 4A is a cross-sectional view of the probe 400 and FIG. 4B shows details of the aperture of the probe 400.

The probe 400 includes an ultrasound transducer 410 positioned at the tip of a shaft 412. The tip of the shaft 412 can be beveled (bevel not shown in FIG. 4A) to aid aiming of the ultrasound beam toward a region of the tympanic membrane, such as the umbo. The external geometry of the transducer 410 does not extend beyond the tip of a probe housing 414. The probe housing 414 can be designed with a speculum aperture 3 mm in diameter to prevent insertion beyond about 10 mm from the tympanic membrane into a region known as the bony portion of the ear canal. Patients can experience considerable discomfort if this area is touched. Additionally, a 3 mm speculum aperture diameter is particularly suitable for patients between 4 and 36 months of age.

The probe housing 414 includes a compliant, silicone rubber speculum 416. The speculum 416 is custom molded to house the ultrasound transducer 410, tubing 418 designed for the introduction of saline, and a relief valve 422 for the prevention of excessive ear effusion buildup. The speculum 416 can be molded to a shape identical to those used for conventional otoscopes, in a range of tip sizes from 2.5 mm and larger in order that pediatric patients of various ages may be examined. A material such as Durometer 70 silicone rubber can be used for the speculum 416 so that a good seal can be created upon insertion of the probe 400. The speculum 416 should allow for the formation of a seal robust enough for the tympanic membrane to be challenged. A perfect seal, however, is not required and may be difficult to achieve when examinations must be made on children who are in serious discomfort and less than cooperative.

In an application where saline is used for coupling the ultrasound to the tympanic membrane, the speculum probe 400 can be used to introduce saline into the external ear canal through the tubing 418, and through rectangular channels 430 molded into the speculum 416. As shown in FIG. 4A, the channels 430 are arranged radially around the perimeter of the transducer 410. Saline pressure is maintained using a low flow-rate peristaltic pump (not shown) coupled to the tubing 418. The tympanic membrane will be challenged via pulsatile flow created by the peristaltic pump and the one-way relief valve 422 located in the speculum housing 414. The pressure in the ear canal is limited to a pre-calibrated level, eliminating the need to measure pressure at each examination. The relief valve 422 allows determination of whether a small displacement of the tympanic membrane is due to ear effusion in the middle ear or an inadequate pressure challenge. The relief valve 422 also reduces the risk of injury to the tympanic membrane in the event of a pump malfunction.

Although not described in detail herein, a similar modified speculum probe design can be employed for applications where an air conduction medium is used. Such modifications can be made without departing from the scope of the present invention. Air pressure can be controlled through the use of a small bulb, and high pressures can be prevented by the use of a two-way relief valve designed for this purpose. In one embodiment, negative pressures will be utilized for an air conduction application, and consequently, it is not anticipated that leakage will present a significant problem.

Figure 5:
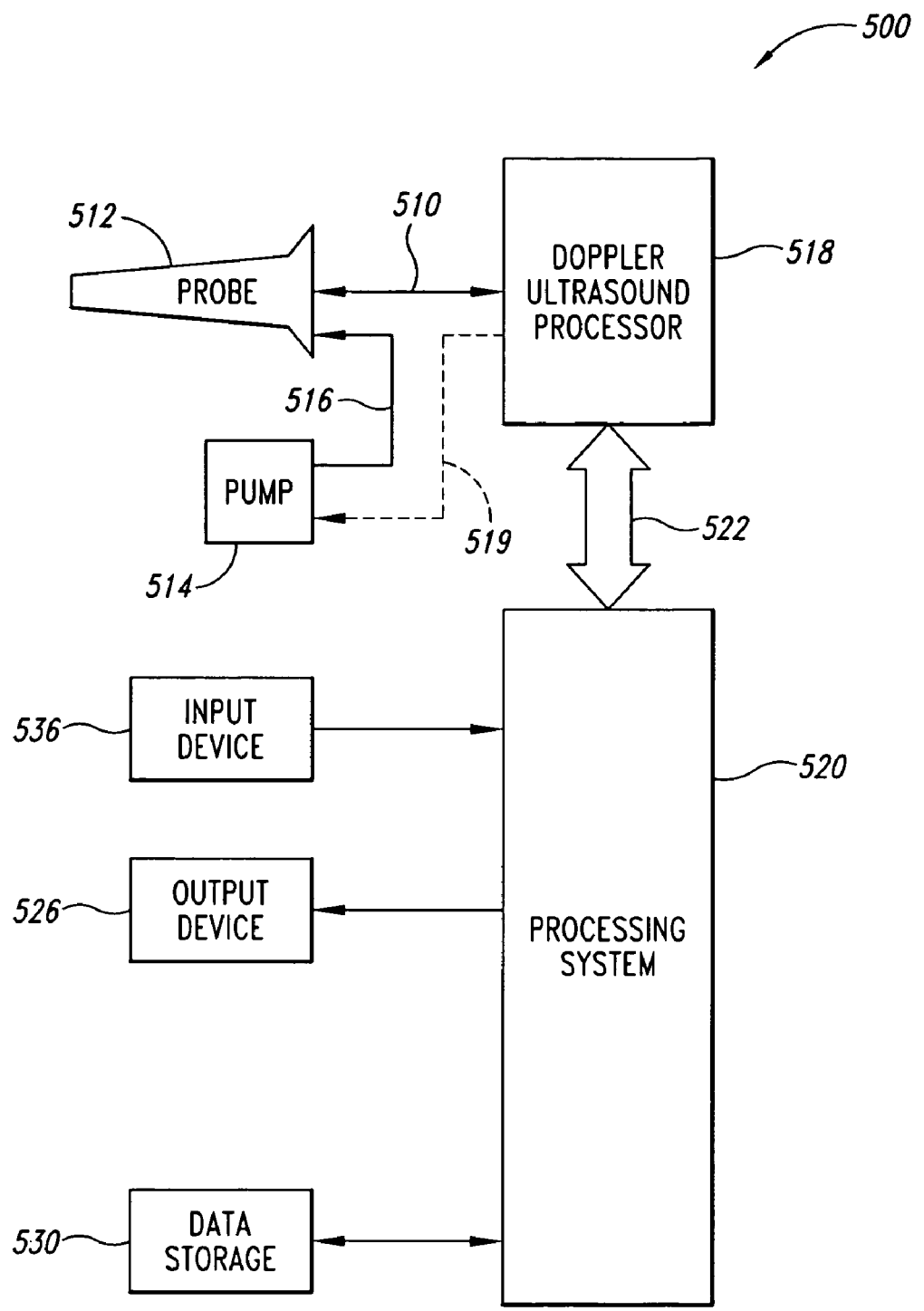
FIG. 5 is a block diagram of an ultrasound system for evaluating ear disorders according to an embodiment of the invention.

FIG. 5 is a functional block diagram that depicts an ultrasound system 500 in accordance with an embodiment of the invention. The ultrasound system 500 includes a Doppler ultrasound processor 518 coupled to an ultrasound probe 512 through cable 510. The speculum probe 400 illustrated in FIG. 4A is an example of a probe suitable for use in the ultrasound system 500. The ultrasound probe 512 is configured for insertion into the ear canal for analyzing the motion of the tympanic membrane, and includes an ultrasound transducer (not shown) for transmitting and receiving ultrasound signals. A pump 514 is connected to the probe 512 through a tube 516 for introducing a coupling medium into the ear canal and for generating pressure perturbations when the probe 514 is inserted into the ear canal. An example of the pump 514 is a variable speed peristaltic or roller pump. Other types of pumps can be used as well. In an alternative embodiment, the pump 514 is operably coupled to the processor 508 to be controlled by the processor 518 to maintain a systematic protocol for challenging the TM and observing its behavior.

As will be described in more detail below, the Doppler ultrasound processor 518 is configured to perform transmit and receive functions, including, generating transmit waveforms to drive the transducer of the probe 512, digitizing echo signals detected by the transducer of the probe 512, and signal processing to generate Doppler shift data representing Doppler shift signals extracted from the receive echo signals.

The Doppler ultrasound processor 518 is coupled to a processing system 520 through a bus 522. The bus 522 can be implemented using conventional computer busses and protocols, for example, the bus 522 can be a universal serial bus ("USB"). The processing system 520 is configured for additional processing of the Doppler shift data provided by the Doppler ultrasound processor 518, and is additionally configured to provide the Doppler ultrasound processor 518 with commands and data for the transmit and receive functions. Additionally, the processing system 520 executes algorithms for performing ultrasound reflectance analysis and ultrasound motion analysis of the tympanic membrane. The processing system 520 can be a host computer system to which the Doppler ultrasound processor 518 is coupled, or alternatively, can represent processing systems included in the Doppler ultrasound processor 518 or in an ultrasound system in which the Doppler ultrasound processor 518.

The processing system 520 is coupled to an output device 526 for providing information and feedback to an operator. Examples of output devices 526 include display devices for providing visual information and audio speakers for providing audible information. A data storage device 530 for storing data, such as data resulting from Doppler shift signal extraction and analysis, is coupled to the processing system 520. Examples of typical data storage devices 530 include hard and floppy disks, tape cassettes, compact disk read-only ("CD-ROMs") and compact disk read-write ("CD-RW") memories, and digital video disks ("DVDs"). The processing system 520 is further coupled to an input device 536, such as a keyboard or a mouse, to allow an operator to interface with the processing system 500.

Figure 6:
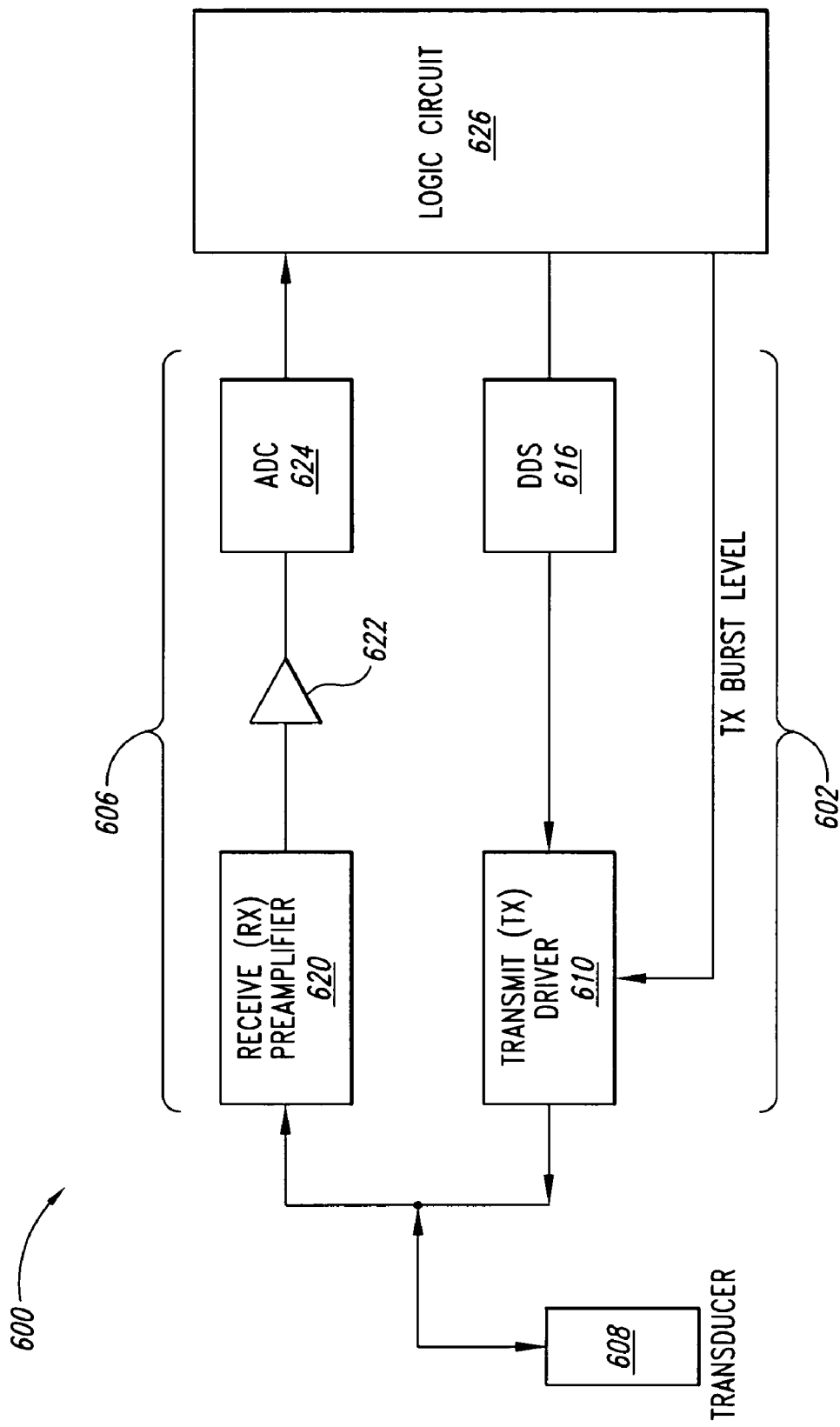
FIG. 6 is a block diagram of a portion of a transmit-receive channel according to an embodiment of the invention of the ultrasound system of FIG. 5.

FIG. 6 illustrates a transmit-receive channel 600 included in the Doppler ultrasound processor 518 of FIG. 5. The transmit-receive channel 600 includes a transmit channel 602 and a receive channel 606 coupled to a logic circuit 626. The logic circuit 626 manages transmit signal generation and initial signal extraction from returned echoes. Although not shown in FIG. 6, the logic circuit 626 is coupled through the data bus 522 (FIG. 5) to the processing system 520, which provides commands and data for the transmit and receive functions of the transmit-receive channel 600.

The transmit channel 602 includes a transmit driver 610 coupled to the logic circuit 626 through a direct digital synthesis ("DDS") circuit 616. The DDS circuit 616 produces an output waveform that is amplified by the transmit driver 610 for driving a transducer 608. The waveform is amplified according to a transmit burst level provided by the logic circuit 626. The ultrasound generated by the transmit channel 602 and the transducer 608 is used to interrogate the tympanic membrane of a patient. Examples of ultrasound that can be used for this application include ultrasound having a pulse repetition frequency ("PRF") of 10 kHz and having a spatial peak temporal average intensity of less than 100 mW/cm$^2$. Various carrier frequencies can be used, including ultrasound having a carrier frequency between 2 MHz and 10 MHz. Higher frequencies are preferable given the relatively short distance between the probe and the target, but this higher frequency must be chosen with understanding of how much attenuation will happen between the probe and the target. The specific ultrasound described herein has been provided by way of example, and ultrasound having characteristics other than that specifically described can be used as well.

The receive channel 606 includes a receive preamplifier 620 coupled to the logic circuit 626 through an amplifier 622 and analog-to-digital converter ("ADC") 624. The receive preamplifier 620 performs bandpass filtering according to the carrier frequency of the ultrasound and provides a filtered signal to the amplifier 622 for amplification. The amplified signal is digitized by the ADC 624, which is capable of sampling at four times the carrier frequency to generate digital echo signal data from which the logic circuit 626 extracts Doppler shift signals. The Doppler shift signals are represented by Doppler shift signal data generated by the logic circuit 626, which as previously discussed are provided to the processing system 520 for analysis.

Figure 7:
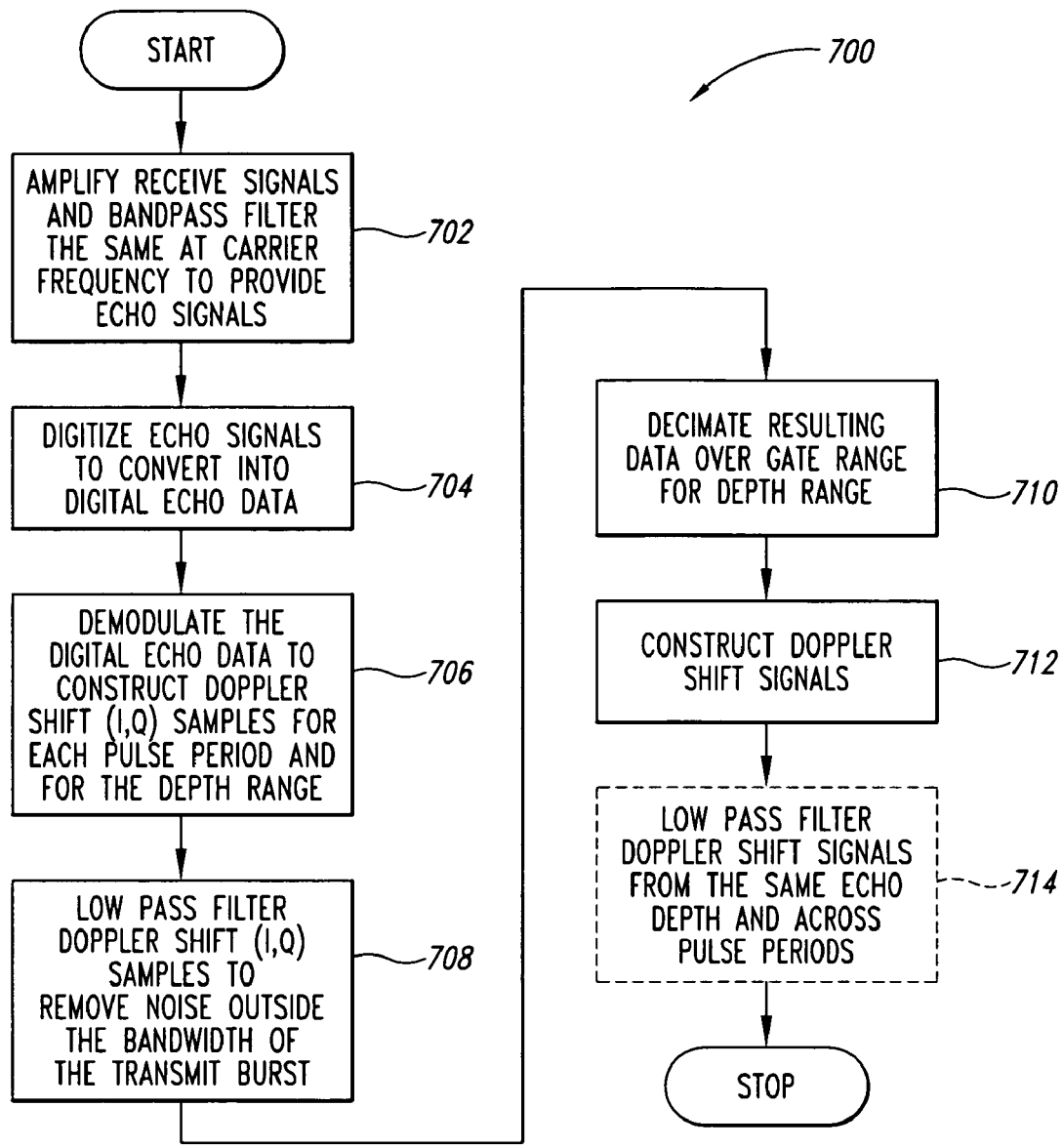
FIG. 7 is a flow diagram of Doppler shift signal processing performed by the transmit-receive channel of FIG. 6.

FIG. 7 is a flow diagram of the data processing performed by the logic circuit 626 for extracting the Doppler shift signals. A more detailed discussion of Doppler shift signal extraction is provided in U.S. Pat. No. 6,196,972 to Moehring, entitled DOPPLER ULTRASOUND METHOD AND APPARATUS FOR MONITORING BLOOD FLOW, which is incorporated herein by reference.

The echo signals are band-pass filtered at the carrier frequency and amplified at step 702. At step 704, for each pulse period of ultrasound, the resulting amplified bandpass-filtered echo signals are sampled at four times the carrier frequency by the ADC 624 to provide digital echo data representing the echo signals. The echo data is demodulated at step 706 to generate Doppler shift (I,Q) samples that stratify a depth range of interest along the ultrasound beam. With a probe inserted in the ear canal and positioned approximately 10 mm from the tympanic membrane, the depth range for observing motion of the tympanic membrane will be centered about a 10 mm depth. As known in the art the "I" value represents a measure of a Doppler shift sample along an "in-phase" or "real" axis of the complex plane and the "Q" value represents a measure of the Doppler shift sample at essentially the same time and position, but on a "quadrature" or "imaginary" axis of the complex plane. The Doppler shift (I,Q) samples are low-pass filtered at step 708 to remove noise outside the bandwidth of the transmit signal. Demodulation and low-pass filtering are performed within each pulse period of ultrasound. Further reference to (I,Q) samples will be understood to refer to Doppler shift data as described above.

The Doppler shift (I,Q) samples can be generated through simple subtraction operations operating on each successive quartet of samples of echo data for a pulse period. Each sample corresponds to digital echo data resulting from sampling the signal output by the amplifier 622 at four-times the carrier frequency. For a quartet of samples, the third value is subtracted from the first value to produce the real part "I," and the second value is subtracted from the fourth value to produce the imaginary part "Q" of a complex Doppler shift (I,Q) sample for an associated depth. The same operation is performed on all quartets of samples of echo data for a pulse period, with each succeeding quartet of points associated with a location of greater depth. The demodulation method blurs the axial resolution by approximately one wavelength of the carrier, but is acceptable in typical applications since one wavelength of the carrier is inconsequential relative to the typical sample volume size associated with medical pulse Doppler ultrasound.

The low-pass filter operation can be performed by taking a series of contiguous gate positions bracketing a desired gate depth, within one pulse period, and performing a dot product with a low-pass finite impulse response ("FIR") filter consisting of a set of coefficients. The number of coefficients or "taps" in the FIR filter will be determined by the sample volume size and the carrier frequency, i.e., how many cycles in a pulse burst. The process of low-pass filtering reduces out-of-band noise from a signal which is sampled across successive pulses at a relatively low frequency (i.e., the pulse repetition rate). The FIR filter is applied to the Doppler shift (I,Q) samples spanning the depth range bracketing a gate to construct one Doppler shift (I,Q) sample for each particular gate for the particular pulse period.

At step 710, the low-pass filtered Doppler shift (I,Q) samples are decimated to carry forward only candidate signals at the depth or at specific depths across a depth range of interest. Doppler shift signals are constructed at step 712 and are represented by Doppler shift data generated by the logic circuit 626. Rather than clutter filtering the Doppler shift signals, as in traditional analysis of blood flow, the "clutter signals" of the Doppler shift signals are analyzed as the signals of interest. These signals generally represent slow moving tissue structure, such as the tympanic membrane. At step 714 a low pass filter may be applied to the Doppler shift signals to eliminate spurious signals or noise from velocities higher than can be reasonably expected from the tympanic membrane motion. For example, each Doppler shift signal may be constructed from Doppler shift samples from the same echo depth and across multiple pulse periods, for example, across 128 pulse periods, which are analyzed to yield an average (I,Q) complex pair. One skilled in the art will appreciate that other low pass FIR filters can be employed, than this example of simple boxcar averaging.

The average (I,Q) value is then concatenated across time with other adjacent average (I,Q) values, and these values are converted from rectangular to polar coordinates. The series of phase angles across this data depicts relative position over time, with one trip around the origin corresponding to motion through one half wavelength towards the probe, and a trip around the origin in the opposite angular direction depicting flow away from the probe. This tympanic membrane position analysis is summarized in the following algorithm:

Calculate mean (I,Q) over set of pulse periods (this may also be a low pass FIR filter calculation as noted above):

$$\overline{(I,Q)}_j = \sum_{k=1}^{N}(I_k, Q_k)/N$$

Where N is the number of pulse periods over which the averaging (or low pass filter operation) is performed, and j is the index of the N-pulse grouping.

Concatenate averaged (I,Q) values over a series of M pulse groupings:

$$P(j) = \overline{(I,Q)}_j,$$

Where j=1 ... M

Convert the elements of P into polar coordinates:

$$\angle P_j = \arctan(Re(P_j), Im(P_j)) \text{ and}$$

$$|P| = Re(P)^2 + Im(P)^2$$

Note that the phase of P, $\angle P_j$, is "unwrapped" so that there are no $2\pi$ discontinuities between adjacent points indexed by j and j+1.

Convert the phase signal to displacement:

$$d_j = \frac{\lambda_L P_j}{4\pi}$$

Where $\lambda$ is the wavelength of the carrier frequency.

As previously discussed, after a determination has been made that ear effusion is present in the middle ear, Doppler ultrasound can be used to analyze the motion of the tympanic membrane in response to pressure perturbations. As motion of the tympanic membrane is induced, the transducer is aimed to a target on the tympanic membrane, such as the umbo, and Doppler shift data is acquired from the target. The clutter portion of the Doppler shift data generated by the logic circuit 626 during this time is representative of motion information for the tympanic membrane. Note the clutter signal is the majority of the signal content. Using the Doppler shift data, the processing system 520 can perform motion analysis as previously described with respect to FIG. 2.

In another embodiment of the invention, a multi-element transducer is used in the speculum probe instead of a single element transducer. The multi-element transducer provides the ability to "aim" the ultrasound to a target on the tympanic membrane by electronic beam steering of the ultrasound. That is, the transmit beam and echoes can be delivered and received along an ultrasound beam axis that is off-axis from a normal (i.e., perpendicular) axis of the face of a transducer. As known, electronic beam steering can be accomplished by using different time delays and different amplitude weights (apodization) for the waveform applied to each transducer element when delivering a transmit pulse and receiving echoes. Note that beam steering can be performed on both transmit and receive: on transmit, the transmit beam is directed to a target, and on receive, the receive signals are analyzed relative to the steering direction using the covariance matrix of the echo signal with respect to different element pairings, as noted below.

Figure 8:
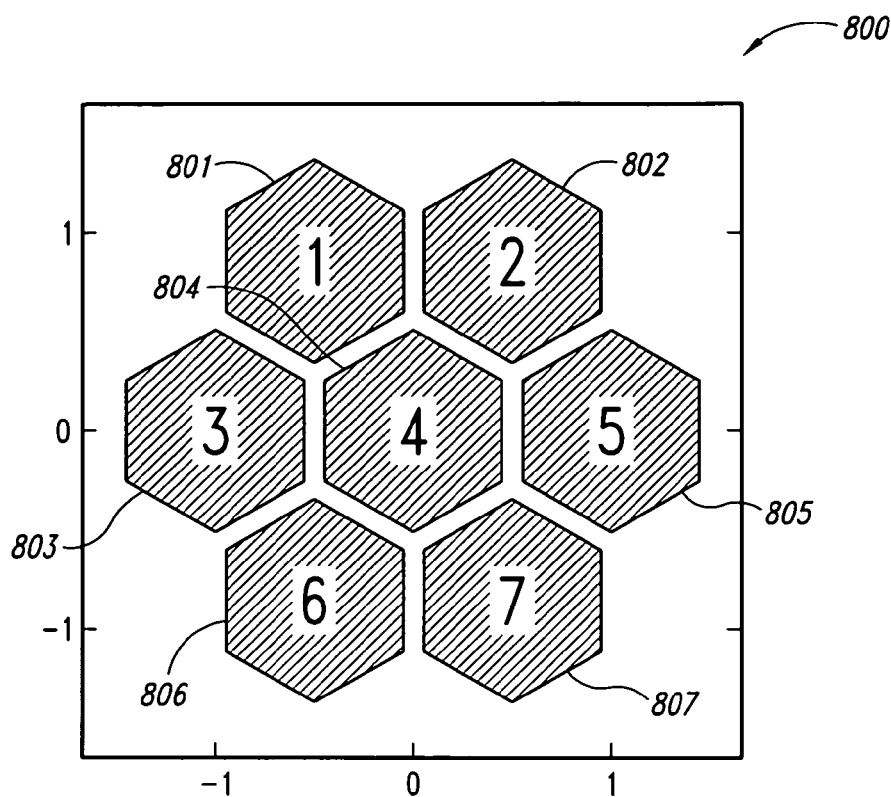
FIG. 8 is a diagram of an arrangement of ultrasound transducers for a multi-element transducer according to an embodiment of the invention.
Figure 9:
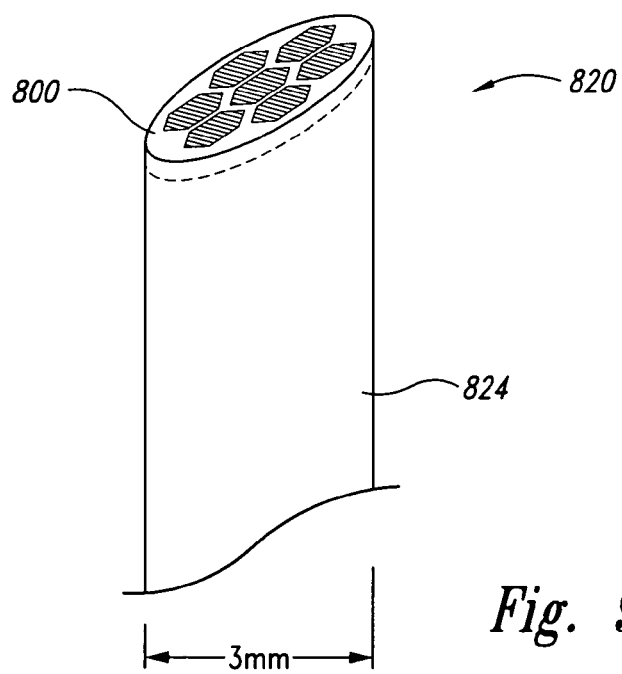
FIG. 9 is a diagram of an ultrasound probe having the multi-element transducer of FIG. 8.

FIG. 8 illustrates an arrangement of a seven-element transducer array 800 for application in analyzing motion of the tympanic membrane. Each element 801-807 is a hexagon, and the overall dimension of the active area is approximately 3 mm. FIG. 9 illustrates a probe 820 having the transducer array 800 positioned on the beveled tip of a shaft 824 which can be inserted into the external ear canal. As known, the axis of the external ear canal extends to intersect with the posterior third of the tympanic membrane. The cant of the tip facilitates positioning of the tip of the probe 820 so that the array 800 naturally looks anterior to the central region of the tympanic membrane. The probe 820 can be incorporated with the speculum probe 400 of FIG. 4A to provide a probe having the canted tip multi-element transducer of the probe 820 and the pressure perturbation functionality of the speculum probe 400. In an embodiment of the present invention, the transducer array 800 is designed to be easily removable to facilitate replacement with a new transducer array 800 after use. In such an embodiment, sterilization issues are significantly reduced since the transducer array 800 can be replaced after a single-use with a new transducer array 800 for use with a new patient. The transducer array 800 can be designed to be manufactured at a low cost. For example, a polyvinylidene fluoride ("PVDF") material can be used for fabricating the transducer elements of the transducer array 800. Such designs and low cost manufacturing techniques are known by those ordinarily skilled in the art, and consequently, in the interest of brevity, a more detailed description is not provided herein.

Figure 10:
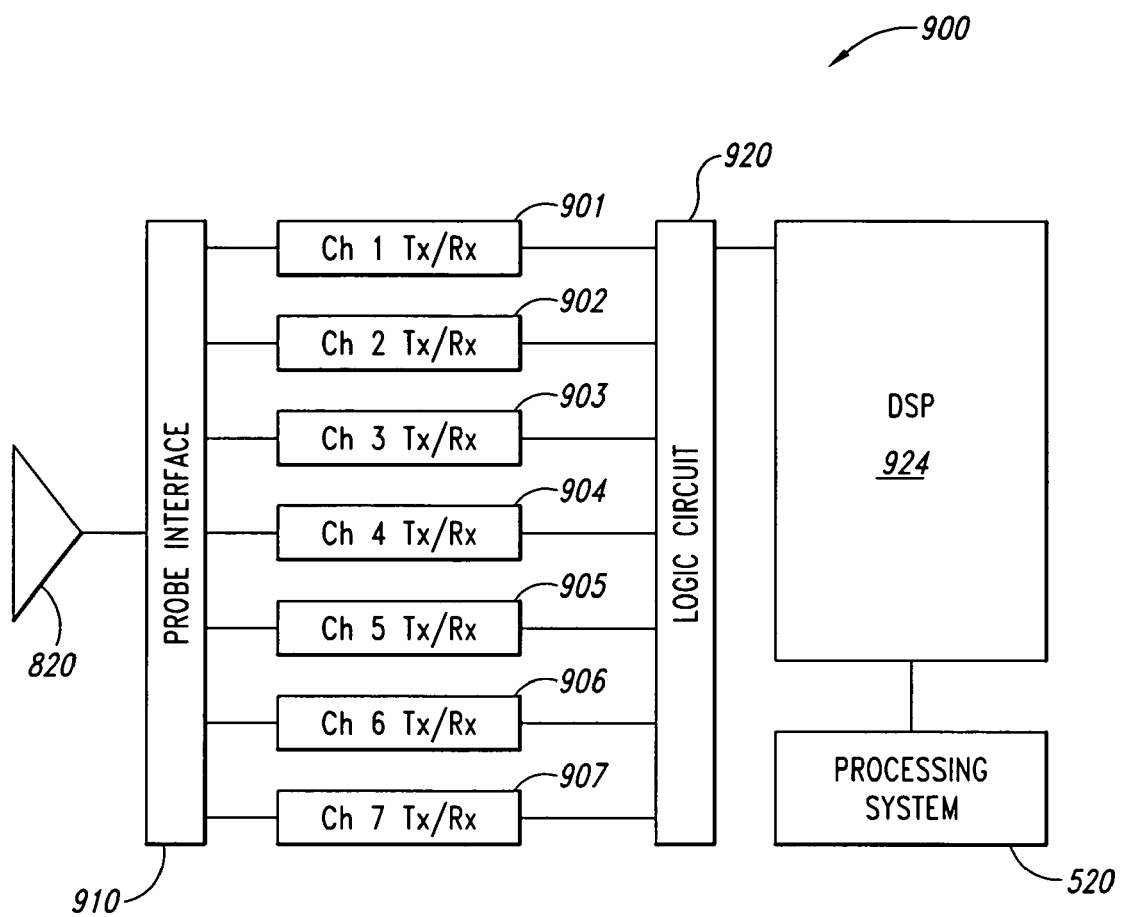
FIG. 10 is a block diagram of a Doppler processing system according to an embodiment of the invention for use with the ultrasound probe of FIG. 9.

FIG. 10 illustrates a Doppler ultrasound processing system 900 for use with the probe 820 that provides electronic beam steering capability. The system 900 includes separate transmit-receive channels 901-907 that are coupled to a respective one of the transducer elements 801-807 through a probe interface 910. The transmit-receive channels 901-907 are similar to the transmit-receive channel 600 previously discussed and have the same transmit and receive functionality. Minor modifications may be necessary for the application in FIG. 10, however, such modifications are known to those skilled in the art. Each transmit-receive channel 901-907 performs the transmit and receive functions for the respective transducer element 801-807 of the probe 820. In place of the logic circuit 626 (FIG. 6) is a logic circuit 920 for performing Doppler signal extraction from the echo signals from each of the transmit-receive channels 901-907. The logic circuit 920 coordinates the transmit and receive functions of the transmit-receive channels 901-907 for electronic beam steering. The logic circuit 920 is operable to control each transmit-receive channel 901-907 to generate a respective waveform having the appropriate timing and amplitude to perform transmit and receive beam steering. The system 900 further includes a digital signal processor ("DSP") 924 coupled to the logic circuit 920 for performing auto-locating and tracking functions. The DSP 924 is also configured to perform motion analysis of the tympanic membrane based on the Doppler shift signals extracted by the logic circuit 920. The DSP 924 is coupled to the processing system 520 via the bus 522.

A more detailed description of an ultrasound system having electronic beam steering and auto-locating and tracking functionality is provided in U.S. patent application Ser. No. 11/152,666 to Moehring et al., entitled MEDICAL DOPPLER ULTRASOUND SYSTEM FOR LOCATING AND TRACKING BLOOD FLOW and filed Jun. 13, 2005, which is incorporated herein by reference. The same principles may be utilized in embodiments of the present invention, with the exception that clutter (tympanic membrane) is the signal of interest, instead of blood flow. Therefore clutter filtering is not part of the algorithm. Significant differences between the above referenced patent application and the present invention are that the clutter rejection in the aforementioned patent application removes brain tissue signals from consideration to leave blood flow as the signal of interest, while tissue motion signals are the signals of interest in the current application. Further, air is not a coupling medium in the former application while it may be a coupling medium in the present application. The target (the tympanic membrane) lies exposed without interposed clutter sources between it and the probe, in the present invention. The covariance matrix of the received, demodulated baseband Doppler shift signal is a vehicle for receive beam steering within the breadth of the transmit burst directivity pattern. This approach is described in the above referenced patent application in detail and is incorporated herein by reference.

The system 900 is configured to analyze 16 different depth sample gates in real-time, which stratify across the anticipated tympanic membrane position at 10 mm depth. The high level signal analysis will identify the gate centered on the tympanic membrane and signal analysis will observe that gate. As the tympanic membrane moves, there will be need to watch migration from gate to gate and follow the signal. The system 900 includes three functional elements in the system: the transmit-receive channels 901-907 that are used to service each transducer element, Doppler signal extraction that is performed by the logic circuit 920, and tissue targeting and motion analysis accomplished by the DSP 924.

Each transducer element of the probe 820 is driven by a pulse burst initiated under the control of the logic circuit 920. As with the transmit-receive channel 600 (FIG. 6), the logic circuit 920 sends pulse burst information to a DDS of each transmit receive channel 901-907. The pulse burst information includes carrier frequency, number of cycles and phase. The DDS of the respective transmit-receive channel 901-907 produces an output waveform which will be amplified (amplification level to be also supplied by the logic circuit 920) to the associated transducer element. The beam steering is facilitated by enabling phase specification down to about $\frac{1}{50}$ of one cycle of the carrier frequency. Steering requirements for particular applications of this technique may vary, and $\frac{1}{50}^{th}$ of one cycle is provided by way of a non-limiting example.

The receiver side of the transmit-receive channels 901-907 provide a narrow band amplification of the received echo which is digitized and provided to the logic circuit 920. As previously discussed, a digitization rate of four times the carrier frequency facilitates extraction of Doppler shift signals. In one embodiment, the transmit-receive channels 901-907 are programmable insofar as the narrow band receive amplification and the A/D digitization rate are adjustable according to the specified carrier frequency. A programmable system allows for a range of carrier frequencies to be applied in observing the tympanic membrane. However, in another embodiment, the carrier frequency of the ultrasound is fixed, allowing for simplification of the transmit-receive channels 901-907.

The digitized received echoes provided to the logic circuit 920 cover the portion of the pulse period associated with round trip to ~6 to 14 mm depth. In the event water is used as a transmission medium, shorter pulse bursts (5 cycles or less) may be necessary in order to insure the transmitter is turned off and quiet (very little ring-down) during the reception of signals from targets so close to the probe. In contrast, if the transmission medium is air, there is the advantage of the physical pulse length in tissue decreasing by the ratio of the speed of sound in air to water, which is about 20 percent. This enables more cycles in the pulse burst from which to do better narrow-band Doppler assessment.

As previously discussed, the Doppler shift signal extraction is done by a simple difference formula applied to every successive quartet of digitized samples. The difference between the first and third sample is the real part of the Doppler shift signal for the given pulse and depth, and the difference between the second and fourth sample is the imaginary part of the Doppler shift signal. Preferably, at least 100 complex Doppler shift values are sampled in the 6 to 14 mm depth range, and the resulting "sample vector" is further filtered to remove out-of-band noise. The resulting signal is sub-sampled at 16 different positions to produce 16 gates stratified across depth range. Doppler shift signal extraction and depth stratification are accomplished by the logic circuit 920. The resulting Doppler shift data is passed to the DSP 924 for high-level signal extraction.

Tissue targeting (beam steering) and motion analysis of the returned echoes are accomplished by the DSP 924. The DSP 924 is configured to repetitively perform a set of tasks for the 16 gates and for every steering direction. These tasks include:

(1) Beam steering to survey a 3 mm radius circular region at 10 mm depth and acquire the coordinates of the tympanic membrane intersecting the "cone" of steered ultrasound beams.

(2) Analysis of signals detected in the middle ear territory, which include from effusion (if present) and from the promontory (to be used as a stationary reference if possible).

(3) Assembly of time history of signals for assessing tympanic membrane motion under the applied pressure challenge.

(4) Detection of artifact events such as vocalization (crying) and probe motions, and rejection of these time periods or separation of signals from artifacts.

The DSP 924 is further configured for automatic targeting of tympanic membrane features using beam steering. The tympanic membrane is located by an auto-locating algorithm by looking for the largest reflections in the depth region, and look for agreement across the different beam steering directions. This agreement does not predicate the signals showing up at the same depth for all steering directions, but rather showing in up a spatially contiguous fashion across the different steering directions. Further, local intersection angle of the tympanic membrane with the ultrasound beam will moderate the return amplitude sensed at the probe. The Doppler-processed echoes will be used for this work. They will contain all the requisite information (motion information and reflectance information) since they will not have been "clutter canceled", and even signals with zero velocity will be fully present.

Figure 11:
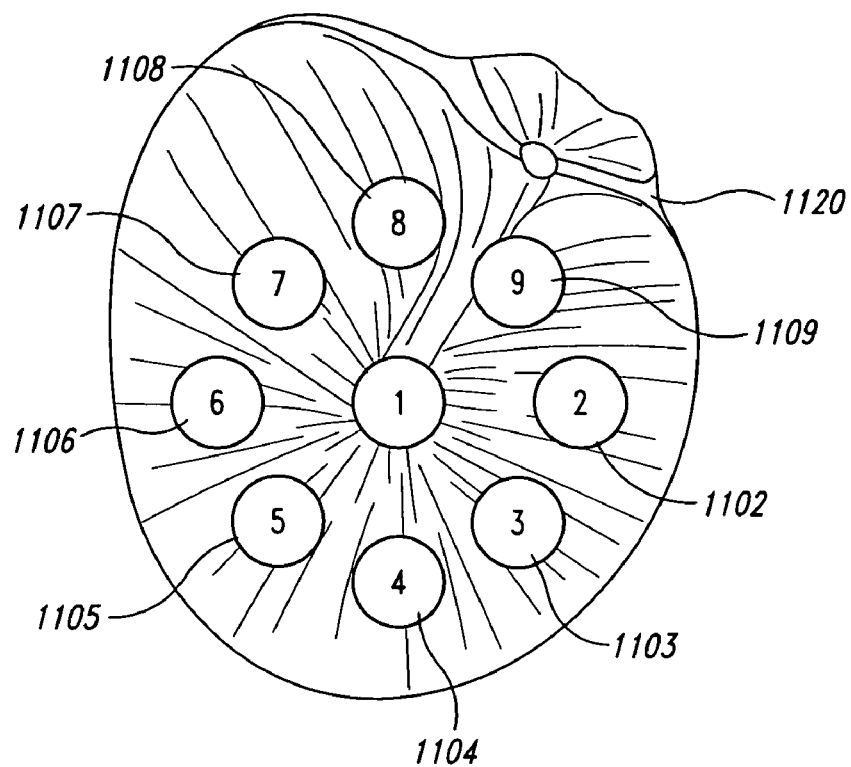
FIG. 11 is a diagram of locations on the tympanic membrane to which ultrasound is electronically steered using the ultrasound probe in FIG. 9 and the Doppler processing system of FIG. 10.
Figure 12:
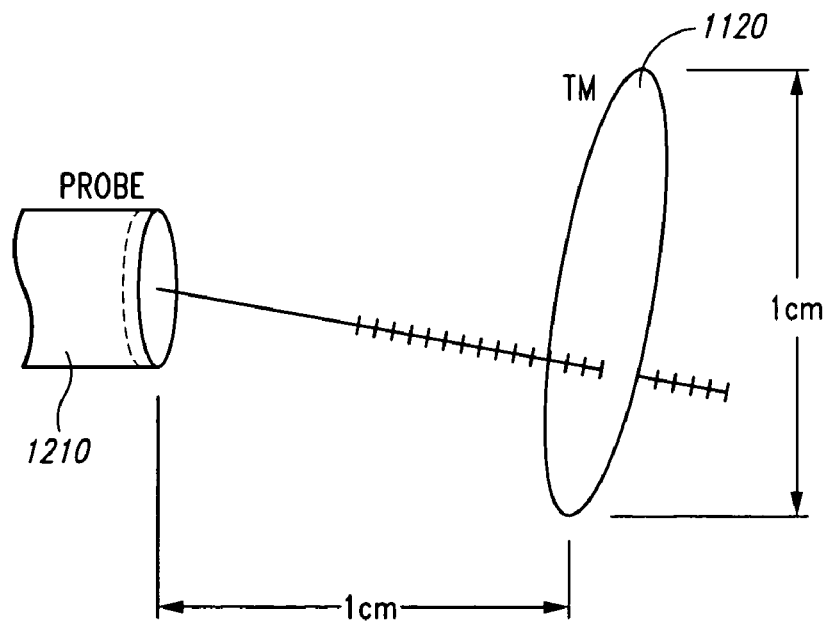
FIG. 12 is a diagram of an arrangement of the ultrasound probe of FIG. 9 relative to the tympanic membrane for interrogating the tympanic membrane with ultrasound.

By utilizing electronic beam steering, the tympanic membrane can be interrogated at a plurality of sample locations. FIG. 11 illustrates an example of the ultrasound beam steered to nine different sample locations 1101-1109 on the tympanic membrane 1120. The degree of steering will be facilitated by using ultrasound having an appropriate carrier frequency. For example, a 2 MHz carrier frequency can be used for saline transmission medium and 1 MHz can be used for air transmission medium. FIG. 12 illustrates the relative arrangement of a speculum probe 1210 and the tympanic membrane 1120 during examination.

Echo information is processed for each beam direction individually in search of an echo in the anticipated depth range (approximately 8 to 12 mm) for the tympanic membrane 1120. This results in a set of echo candidate information for each location 1101-1109 (FIG. 11). The ensemble of nine sets of echo candidate information are reviewed for congruence with understanding of tympanic membrane structure. That is, the ensemble of echo candidate information acts like a spatially contiguous group of targets, which may be at different depths for different beam directions, and moves in concert under an applied challenge. When the ensemble of echo candidate information exhibits these characteristics, it is assumed the speculum probe 1210 is appropriately aimed toward the tympanic membrane 1120 and information for the moving tympanic membrane can be obtained for analysis. The speculum probe 1210 may need to be reoriented until appropriate aiming is achieved.

The beam steering directions will be accomplished in real time, which will enable motion signals from all observed sample locations 1101-1109 on the tympanic membrane 1120 to be acquired under the same brief interval. A target depth of 10 mm corresponds to a pulse-echo time period of 13 µs in saline and 60 µs in air. A 220 µs pulse period should provide sufficient margin for extraneous echoes before a new transmit pulse is launched, and corresponds to 500 pulses per second for each of the nine sample locations 1101-1109. The maximum Doppler shift (with spectral unwrapping, and using 2 MHz carrier for saline and 1 MHz carrier for air as noted above) is 18 cm/s for saline and 8 cm/s for air transmission medium. This can be increased by going to fewer steering directions when the motion stimulus is applied. Hence there may be a target location mode with more transmit directions applied and a "motion stimulus" mode with fewer transmit directions.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for analyzing motion of the tympanic membrane, comprising:
   inducing motion of the tympanic membrane;
   applying ultrasound to the moving tympanic membrane; and
   extracting Doppler shift signals from the echo signals resulting from the ultrasound to analyze displacement of the tympanic membrane due to the induced motion to categorize viscosity of ear effusion, a displacement less than a displacement threshold indicative of ear effusion of a first viscosity and a displacement greater than the displacement threshold indicative of ear effusion of a second viscosity less than the first viscosity.

2. The method of claim 1 wherein inducing motion of the tympanic membrane comprises:
applying a pressure impulse to the tympanic membrane.

3. The method of claim 2 wherein applying a pressure impulse to the tympanic membrane comprises:
introducing a liquid coupling medium into the ear canal; and
generating a pulsatile flow of the liquid coupling medium.

4. The method of claim 3 wherein introducing the liquid coupling medium comprises introducing saline into the ear canal.

5. The method of claim 1 wherein extracting the Doppler shift signals comprises extracting the Doppler shift signals to analyze velocity of the tympanic membrane due to the induced motion.

6. The method of claim 1 further comprising applying imaging ultrasound and processing the echo signals to provide an image and observing the image versus both depth and time.

7. A method for examining an ear of a patient, comprising:
applying ultrasound to a portion of the ear;
detecting the presence of a fluid in the middle ear from reflected ultrasound;
if a fluid is detected, analyzing Doppler shift signals to provide a measure of motion response of a tympanic membrane in response to a perturbation inducing motion of the tympanic membrane; and
categorizing the fluid based at least in part on the measure of motion response, the measure greater than a threshold indicative of a first fluid category and a measure less than the threshold indicative of a second fluid category.

8. The method of claim 7 wherein the fluid comprises an ear effusion and wherein categorizing the fluid comprises categorizing a viscosity of the ear effusion.

9. The method of claim 7 wherein detecting the presence of a substance in the middle ear from the reflected ultrasound comprises:
analyzing signal amplitude of the reflected ultrasound to determine the presence of the substance.

10. The method of claim 9 wherein analyzing signal amplitude of the reflected ultrasound comprises:
comparing the signal amplitude to a threshold;
in response to the signal amplitude being less than the threshold, indicating the presence of a substance.

11. The method of claim 7 wherein analyzing Doppler shift signals to analyze the motion response of a tympanic membrane comprises:
analyzing Doppler shift signals to analyze displacement of the tympanic membrane in response to the perturbation.

12. The method of claim 7 wherein analyzing Doppler shift signals to analyze the motion response of a tympanic membrane comprises:
analyzing Doppler shift signals to analyze velocity of the tympanic membrane in response to the perturbation.

13. The method of claim 7, further comprising processing the reflected ultrasound to provide an image and observing the image versus both depth and time.

14. A method for examining a patient for an ear disorder, comprising:
applying reflectance ultrasound to determine the presence of ear effusion in a middle ear;
inducing motion of a tympanic membrane if ear effusion is present;
applying Doppler ultrasound;
extracting Doppler shift signals from echo signals; and
analyzing the Doppler shift signals to categorize viscosity of the ear effusion based at least in part on the velocity of the tympanic membrane in response to the induced motion, the ear effusion categorized as a first viscosity in response to a velocity greater than a velocity threshold and the ear effusion categorized as a second viscosity higher than the first viscosity in response to a velocity less than the velocity threshold.

15. The method of claim 14 wherein applying Doppler ultrasound comprises:
electronically steering ultrasound in a plurality of directions to interrogate the tympanic membrane; and
extracting Doppler shift signals from echo signals from the plurality of directions.

16. The method of claim 15, further comprising:
processing the Doppler shift signals to automatically locate a target on the tympanic membrane and track the target while the tympanic membrane is in motion.

17. An ultrasound system for examining an ear of a patient, comprising:
an ultrasound probe operable to induce motion of a tympanic membrane and further operable to provide ultrasound to the moving tympanic membrane and receive echo signals therefrom;
an ultrasound signal processing circuit operable to process the echo signals to detect the presence of a fluid in the middle ear, and if a fluid is detected, derive Doppler shift signals from the echo signals to provide a measure of motion response of the tympanic membrane due to the induced motion to characterize categorize viscosity of ear effusion, the measure of motion response greater than a threshold indicative of a first fluid viscosity and a measure less than the threshold indicative of a second fluid viscosity higher than the first viscosity.

18. The ultrasound system of claim 17, further comprising a saline source and a pump for introducing the saline into the ear canal and generating a pulsatile flow of the saline.

19. The ultrasound system of claim 17 wherein the fluid comprises ear effusion and the ultrasound signal processing circuit is operable to process the Doppler shift signals and categorize the ear fluid based on viscosity.

20. The ultrasound system of claim 17 wherein the ultrasound probe comprises a multi-element transducer and the ultrasound system further comprises:
a beam forming circuit operably coupled to the multi-element transducer to electronically steer ultrasound in a plurality of directions to interrogate the tympanic membrane with ultrasound.

21. The ultrasound system of claim 20 wherein the ultrasound signal processing circuit is further operable to extract Doppler shift signals from the echo signals from the plurality of directions and process the Doppler shift signals to locate a target on the tympanic membrane track the target while the tympanic membrane is in motion.

22. The ultrasound system of claim 21 wherein the beam forming circuit comprises a plurality of transceiver channels, each channel operably coupled to a respective element of the multi-element transducer.

* * * * *